United States Patent [19]

Beckman

[11] 4,115,230
[45] Sep. 19, 1978

[54] PARTIAL OXYGEN MEASUREMENT SYSTEM

[76] Inventor: Paul Beckman, 944 Henrietta Ave., Huntingdon Valley, Pa. 10096

[21] Appl. No.: 757,207

[22] Filed: Jan. 6, 1977

[51] Int. Cl.² ............... G01N 27/28; G01N 27/46; H05B 3/58
[52] U.S. Cl. ............... 204/195 R; 204/195 B; 204/272; 219/535; 324/29
[58] Field of Search ............... 204/1 Y, 195 R, 195 B, 204/272; 324/29; 128/2 G, 2 E, 2.1 E; 219/301, 535; 165/46

[56] References Cited

U.S. PATENT DOCUMENTS

| | | | |
|---|---|---|---|
| 3,223,608 | 12/1965 | Hersch | 204/195 R |
| 3,453,417 | 7/1969 | Hummel | 219/536 |
| 3,925,183 | 12/1975 | Oswin et al. | 204/195 R |

*Primary Examiner*—G. L. Kaplan
*Attorney, Agent, or Firm*—Paul Maleson; Morton J. Rosenberg

[57] ABSTRACT

A partial oxygen pressure measuring system for quantitating the amount of dissolved oxygen in solution of a fluid sample. The system includes a sensor electrode within which a volume of fluid whose oxygen is to be measured is inserted. The sensor has a silver chlorided tube with an insulated nickel wire of reduced diameter passing coaxially and internal thereto. The nickel wire terminates in an end section which is platinum plated to form a polarizing surface. Both the silver chloride tube and wire pass external to the sensor and are electrically coupled to a pair of contact rings which represent cathode and anode junctions respectively. A biasing voltage is placed across the contact rings to form a circuit path through the wire, platinum coated surface, fluid sample and base reference silver chlorided tube in order to determine the current flow which is a measure of the oxygen level in the fluid sample. The system further includes a resistance thermal device in combination with a heater assembly in order to heat the fluid sample to a predetermined temperature and maintain it for a predetermined time interval. Both the voltage application and the heating assembly are initiated simultaneously by the closing of a lid of a portable housing within which the sensor is inserted. After a time interval, subsequent to the housing lid closure, a display of the partial oxygen pressure in the fluid sample is provided.

55 Claims, 10 Drawing Figures

U.S. Patent  Sept. 19, 1978  Sheet 1 of 5  4,115,230
FIG. 1
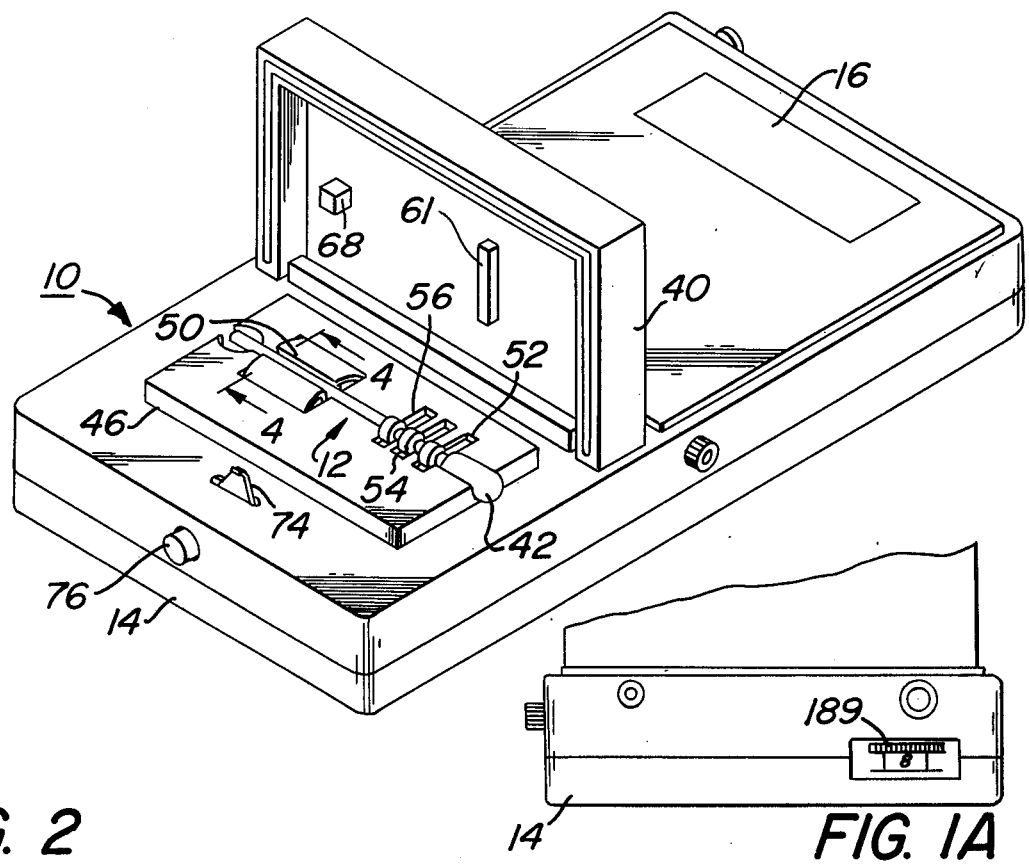
FIG. 2
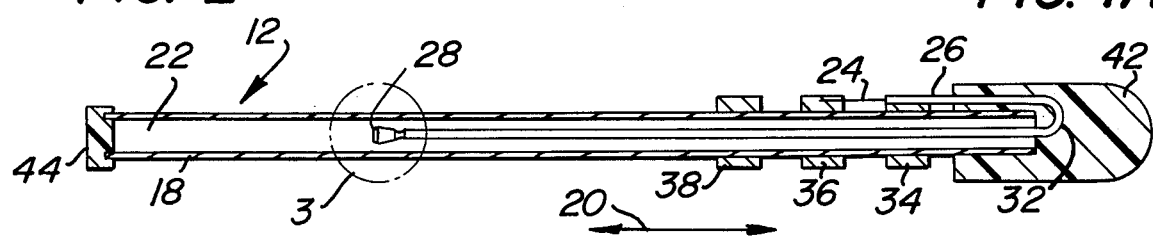
FIG. 1A
FIG. 3
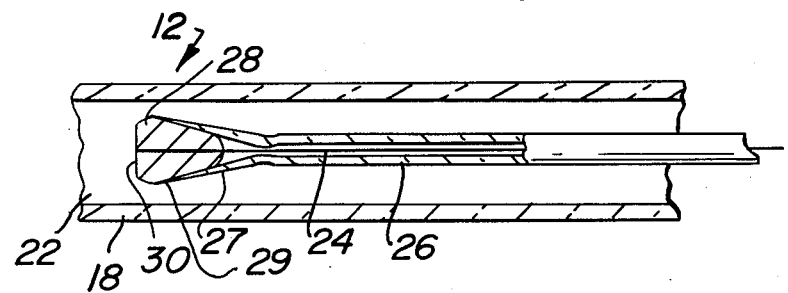

PARTIAL OXYGEN MEASUREMENT SYSTEM

BACKGROUND OF THE INVENTION

1. FIELD OF THE INVENTION

This invention relates to systems for measuring particular quantities of compositions in a fluid. In particular, this invention pertains to systems for measuring partial oxygen pressure in fluid samples. More in particular, this invention relates to a portable system for quantitating the amount of dissolved oxygen in solution within a fluid sample. More in particular, this invention relates to a measuring system utilizing an open type electrode sensing device. Still further, this invention relates to a system for analyzing fluid samples in a closed volume chamber by passage of current through a predetermined circuit within an open type electrode sensor. Additionally, this invention relates to a measuring system which simultaneously heats the fluid sample to a predetermined temperature and measures the current being passed through an electrode sensor containing the fluid sample in order to provide a readout of the amount of predetermined constituents contained in the fluid sample. Still further, the invention pertains to a measuring system where a fluid containing sensor is inserted into a hand held housing and actuation of the measuring system is dictated by application of the closing of lid of the housing to provide heating and current flow to the electrode sensor. Additionally, this invention relates to a measuring system which utilizes a wrap around type of heating assembly to maximize the heat transferred to a fluid sample while minimizing the temperature gradients created in the fluid sample.

2. PRIOR ART

Measuring systems for quantitating the amount of dissolved oxygen in fluid samples are known in the art. In some prior systems, such as those commonly referred to as a Clark electrode, a base reference and a cathode are placed behind a permeable membrane defining a chamber having an electrolyte contained therein. The gas to be measured then diffuses through the membrane and such is electrically and physically isolated in the solution, Appropriate currents are passed through the system and readings of the quantity of gas are measured. However, in such like prior systems, the electrolyte may be found to dry out. The electrolyte must then be replaced which is a difficult and time consuming procedure. Additionally, in such prior systems the membrane has been found to rupture and replacement of such has been found to additionally add to the costs of measuring fluid samples with such prior art systems.

Additionally, in prior systems of the permeable membrane type, consumption of the oxygen by the electrode may form a diffusion gradient in the liquid sample external to the membrane. Such diffusion gradients lead to erroneous readings of the percentage of the constituent being measured in the fluid sample.

In some such prior systems the temperature of the fluid sample has not been easily controlled within sufficiently restrictive tolerance ranges so as to provide constant reproducable readings of fluid sample measurements.

In other prior systems where fluid sample temperatures were maintained constant, circulating pumps were necessary to restrict temperature excursions. This increased the hardware cost and eliminated the possibility of producing a portable measurement system.

In other prior systems, where open electrodes were utilized, protein poisoning due to relatively long electrode/fluid sample exposure time, was found to be a major disadvantage. The resulting protein poisoning reduced the accuracy and associated repeatability of the fluid sample measurements.

SUMMARY OF THE INVENTION

A fluid measuring system for quantitating the amount of particular constituents contained in a fluid. The system includes a sensor device having a chamber containing the fluid. The sensor device is inserted within a housing in predetermined positional relationship therewith. A thermostatic control mechanism within the housing heats and maintains the fluid within the chamber at a predetermined temperature. Electronic circuitry applies current to the sensor device for measurement of the particular constituents contained in the fluid.

BRIEF DESCRIPTION OF THE FIGURES

FIG. 1 is a perspective view of the system housing;

FIG. 1A is a partial cut away view of an elevation view of the system housing;

FIG. 2 is an elevational view of the electrode sensor;

FIG. 3 is an elevational view of the electrode sensor showing a cut away view of the internal working portions thereof;

DESCRIPTION OF THE PREFERRED EMBODIMENTS

Figure 4:
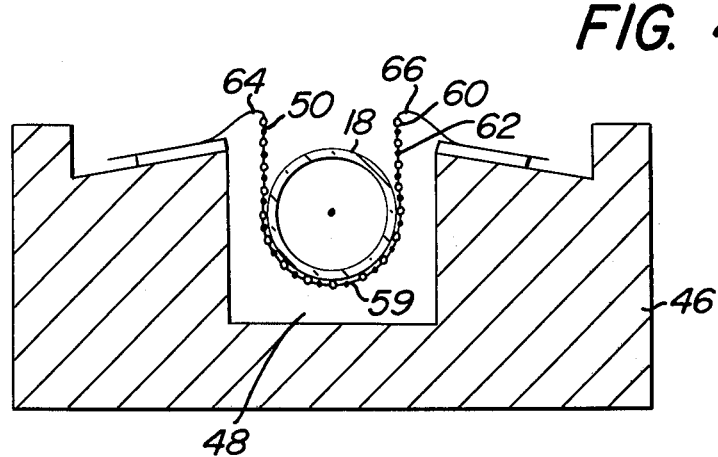
FIG. 4 is a sectional view of the thermostatic control and heat mechanism taken along the section lines 4-4 of FIG. 1.

Referring now to FIGS. 1-6 there is shown fluid measuring or oxygen analyzing systen 10 for measuring the dissolved oxygen content of a fluid sample. In overall concept, a fluid sample such as blood is drawn internal to sensor or oxygen sensing electrode 12 which is then capped or otherwise sealed in order to negate the possibility of the fluid sample egressing. Sensor 12 is then inserted into a compartment within system housing 14 for initiation of a sequence of events resulting in an indication of the dissolved oxygen content of the fluid sample being provided in display 16.

Once sensing electrode 12 is inserted into system housing 14, a proportionally controlled heater (to be described in following paragraphs) is activated in order to thermally drive the fluid within sensor 12 to a predetermined temperature. Additionally, and occurring simultaneously, current flowing in biased polarographic electrode 12 is amplified and processed for display. Appropriate circuitry inhibits the display of the oxygen values being calculated for a predetermined time in order that thermal and chemical equilibrium may be achieved. Subsequent to the predetermined time, the final reading processed and calculated is held and display 16 is enabled in order to allow the operator to record the value of dissolved oxygen.

Oxygen sensing electrode or bulb sensor 12 includes extended glass tube 18 having an internal volume, at least a portion of which forms chamber 22 within which the fluid sample is maintained. Outer or glass tube 18 extends in longitudinal direction 20 and may be formed of a standard glass composition, not important to the inventive concept as is herein described, with the exception that the glass composition be chemically inert when taken with respect to the contained fluid sample.

Additionally, glass rube 18 may include an outer diameter approximating 0.60 tube inches and an extension in longitudinal direction 20 of approximately 2.0 inches. Such dimensional considerations, although not pertaining to the inventive concept, are provided to clarify the relative sizes of system 10 under consideration.

Silver tube or anode electrode element 26 extends in direction 20 within tubular element 18 into chamber 22. Additionally anode electrode element 26 has chloride coating formed an external surface thereof in order to form a stable reference. By providing a chloride coating, silver tube 26 will not polarize and thus becomes a stable reference electrode. In this manner, when a bias voltage is applied to silver tube or anode element 26, substantially no current will flow in the absence of oxygen. Thus, with the formation of this type of stable reference electrode, there is substantially zero current flow with a corresponding zero oxygen content in the fluid sample being measured.

Nickel wire element or cathode electrode element 24 having insulation surrounding it, extends coaxially within silver tube 26 and passes throughout a portion thereof as is shown in FIGS. 2 and 3. Silver chlorided tube 26 includes flared end section 27 producing an increased diameter end plane surface 29 when taken with respect to the remaining internal diameter of tube 26.

Initially, insulated nickel wire is inserted through tube 26 and extends beyond end surface 29. A drop of epoxy element 28 is inserted adjacent flared section 27. At this time epoxy element 28 is substantially in the liquid phase and encompasses wire element 24. Epoxy element 28 acquires a somewhat spherical contour prior to complete hardening.

Epoxy element 28 has been successfully formed of a combination of an epoxy resin composition having a tradename Aralydite in combination with a hardener and an accelerator. The Aralydite composition has a commercial designation CY 170 and is produced by Ciba-Geigy Corporation. The hardener and accelerator have commercial designations of No. 917 and DY-065 respectively and is further produced by the aforementioned corporation. In order to produce a bubble free, gas tight, inert and waterproof epoxy element 28, 100 parts of Aralydite, 105 parts of hardener No. 917 were mixed with 12 parts of accelerator DY-065. The combination was air dried and cured at approximately 125° C. resultinhg in a hardened component composition.

A microtome or other extremely sharp instrument is utilized to shear both epoxy element 28 and wire 24 in a direction normal to the extended length of wire 24. Cutting in this manner forms epoxy element planar face 30 and additionally provides for an undistorted exposure of bare planar end surface of wire 24. As can be seen in FIGS. 2 and 3, wire 24 is peripherally surrounded and guarded by potting or epoxy element 28. However, the end surface of wire 24, having been sheared is exposed to the surrounding environment. The shearing step or action is highly important due to the fact that a clean shear defines the end surface cross sectional area that essentially becomes the cathode of bulb sensor 12. The end surface of wire 24 is then plated with platinum in order to form the active surface providing for the cathode of system 10.

Thus, epoxy element 28 having planar end face 30 is formed over an end surface of silver chlorided tube 26 and insulated nickel wire 24 extending internal and co-axial with silver chlorided tube 26 in longitudinal direction 20. Tube 26 and insulated wire 24 in combination are then contoured into U-section 32. The combination of epoxy element 28, tube 26, and insulated wire 24 is then inserted longitudinally within glass tube 18 and extends external thereto through U-section 32 as is clearly seen in FIG. 2. Extending around the periphery of glass tube 18 as is shown in FIG. 2, is first, second and third electrical contacts 34, 36 and 38 respectively.

Contactors 34, 36, and 38 may be split ring type elements in order that wire 24 and silver chlorided tube 26 may be inserted in the discontinuous portion of the contactors 34 and 36. As is seen in FIG. 2, an insulation stripped section of wire 24 is brought into contact with contactor 36 and tube 26 is inserted into contact with first electrical contactor 34. Electrical contact or continuity may be formed by insertion of a silver epoxy into the discontinuous portions of contactors 34 and 36, or in some like manner not important to the inventive concept as is herein defined.

Nickel wire 24 prior to insertion into second electrical contactor 36 is stripped of its insulation in order that electrical contact may be made by the silver epoxy filling the opening in the split ring within which the stripped wire 24 has been inserted. Thus, rings 34 and 36 now constitute electrical connections with ring 36 performing the function of a cathode and ring or contactor 34 performing the function of an anode. Third electrical contactor 38 does not have to be split in contour and is utilized as an actuator so that when bulb sensor 12 is inserted into housing 14 and lid 40 is closed, initiation of the electrical sequence of events may be provided.

As will be seen in following paragraphs and more fully described, closing of housing lid 40 applies a downward pressure to oxygen sensing electrode or bulb sensor 12 and firmly positions sensor 12 in heater and contact apertures. Once this is done there is a closure of a pair of contacts which serve as a main power switch for system 10. Electrical connection is made to the anode and cathode of the polarographic sensor 12 through spring contacts against rings 34 and 36 respectively surrounding glass tube 18. A substantially constant potential of 0.7 volts is applied between anode junction 34 and cathode junction 36 with the cathode being negative. This causes the platinum surface defined by the planar end surface of wire 24 to polarize. The chemical reduction of dissolved oxygen in the fluid within chamber 22 in the vicinity of the cathode constitutes the only current which flows. As is well known in the art, the magnitude of the current is then directly proportional to the oxygen content of the fluid in the vicinity of the cathode.

Bulb element 42 having a recess for insertion of glass tube 18 and silver chlorided tube 26 in combination with insulated wire 24 is utilized to provide a means whereby fluid may be drawn into chamber 22. Bulb element 42 may be formed of a silicon type compound, rubber, or some like resilient composition not important to the inventive concept as is herein provided.

Another device which may be utilized to draw fluid internal to chamber 22 is through a reversibly moveable plunger commonly used in hyperdermic needles. In such cases, the plunger device would replace bulb element 42 as the fluid intake mechanism.

Additionally, cap element 44 may be formed to interface with an opposing end of glass tube 18 in secured contact through force fitting or some like technique. Cap element 44 may similarly be formed of a silicon compound or rubber composition or other like material not important to the inventive concept with the exception that the composition of cap element 44 should be generally inert with respect to the fluid sample drawn into chamber 22.

In overall concept, when oxygen analyzing system 10 is to be used in conjunction with the removal of blood from a human, an arterial puncture is provided by an instrument used for such purposes and generally not part of the subject invention. The blood is then inserted into an appropriate container. Electrode sensor 12 is inserted into the blood within the container subsequent to bulb element 42 being compressed. Resilient bulb 42 is released and blood is drawn into chamber 22. Cap element 44 is inserted over an end section of glass tube 18 in order to capture the blood within chamber 22. Sensor 12 is now ready for insert into system housing 14 as will be described in following paragraphs.

Referring now to FIGS. 1 and 4-6 there is shown positioning block 46 for insert of bulb sensor 12 within system housing 14. Positioning block 46 includes heater sensor assembly well 48 within which thin film heater assembly 50 is positioned. Additionally, contactor wells 52, 54 and 56 are formed within block 46 for insertion of contactors 34, 36 and 38 respectively.

As will be explained in following paragraphs, contactor 38 is a switch contact which initiates the timing assembly circuit upon closure of lid 40. Upon closure of lid 40 contactors 34 and 36 representing the anode and cathode respectively, form the appropriate electrical contact and provide the circuit for measurement of the dissolved oxygen content as has hereinbefore been described.

Heater and thermostatic control assembly 50 is utilized to initially heat the fluid contained within chamber 22 to a predetermined temperature and maintain that temperature throughout the partial oxygen measuring time interval. In the case of human blood, heater and thermostatic control assembly 50 heats the blood to a temperature approximating 98.6° F. (37° C.) and maintains such temperature throughout the partial oxygen pressure reading time.

Figure 5:
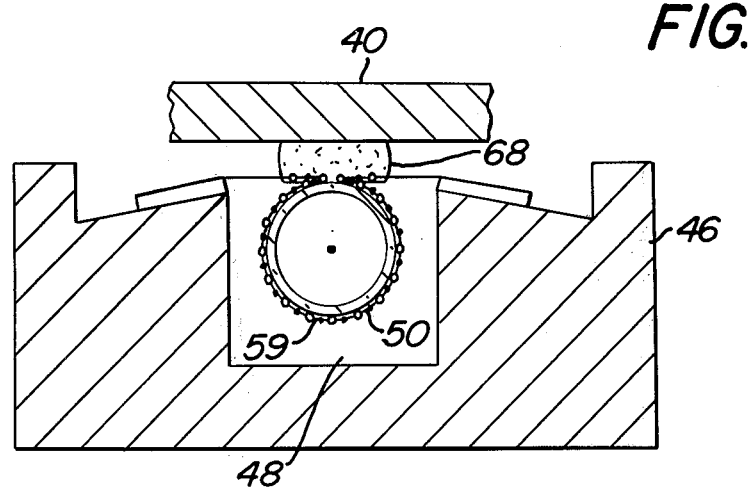
FIG. 5 is an elevational view of the thermostatic and heater control mechanism after the lid of the system housing is closed.
Figure 6:
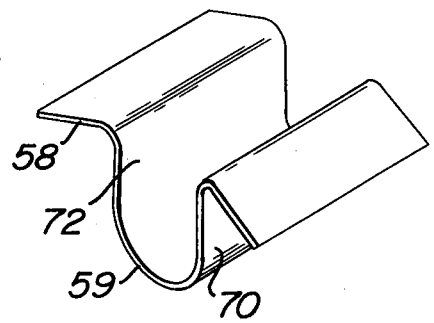
FIG. 6 is a perspective view of the heating coil of the heater and thermostatic control mechanism.

Heater and thermostatic control assembly 50 is formed of foil member 58 which is contoured into an inverted omega configuration as shown in FIG. 6. Etched in a zig-zag pattern extending in longitudinal direction 20 within foil 58 are heater wires 60 and fine resistance thermometer wire 62 as is shown in FIGS. 4 and 5. Heater wires 60 are relatively heavy forming approximately a 50 ohm heater. Formed between respective wires 60 are resistance thermometer wires 62 which are used to sense the temperature around the external surface of glass tube 18.

Foil member 58 is formed into an inverted omega type contour and includes uppr transversely opposed sections 64 and 66 which as will be seen may be resiliently formed around glass tube 18 upon closure of lid 40.

Initially, glass tube 18 is inserted into foil member 58 as is shown in FIG. 4. Lid 40 may include hard rubber shoe element 68 which compressively interfaces with an end portion of glass tube 18. Element 68 only contacts tube 18 and does not contact member 58. As tube 18 is forced downwardly against foil member lower surface 59, such is displaced in a downward direction within well 48. Due to the resilient nature of foil member 58 which may be formed of a capton substrate, it has been found that opposing vertically directed walls 70 and 72 of foil member 58 are deflected and wrap themselves around the peripheral boundary surface of glass tube 18 as is shown in FIG. 5. Opposing transverse ends 64 and 66 are thus brought into the vicinity of the surface of tube 18. Thus, it is seen that heater wires 60 and resistance thermometer wires 62 are placed into contiguous contact throughout a substantial surface perimeter of tube 18 when lid 40 is closed. In this manner, there is a minimization of thermal losses with a maximization of heat transfer passing internal to tube 18. Additionally, with the encompassing of tube 18 throughout a substantial segment of the circular contour, it has been found that there is a minimization of thermal gradients applied to the fluid contained within chamber 22. With this type of configuration and element contour, the blood or other fluid sample contained within chamber 22 is substantially maintained at constant temperature throughout chamber 22. Additionally shoe element 61 is aligned with contactor 38 in a manner such that when lid 40 is closed, contactor 38 is deflected downward to initiate the electrical circuitry.

By providing resilient foil member 58 of heater and thermostatic assembly in the contour as shown in FIGS. 4-6 and hereinbefore described, heat may be inserted to the fluid sample in a generally symmetrical radial fashion. Thus, thermal gradients are minimized and a maximization of heat is inserted to the fluid in order to bring the fluid sample to predetermined temperature conditions in a short interval of time. One of the very important parameters in determining the partial oxygen pressure of the fluid sample is the accurate knowledge of the temperature of the fluid sample within chamber 22. Through this type of foil construction, it has been found that temperatures may be maintained within an approximate tolerance range of plus or minus tolerance of at least 0.1° C. Additionally, since the fluid sample is substantially surrounded by heater wire 60 and resistance thermometers 62 there is a minimization of heat losses and the temperature of the fluid is generally constant throughout the cross sectional area to provide an accurate reading.

Actuation of heater and thermostatic control assembly 50 is initiated through closure of lid 40 responsive to contactor 38 being compressed into well 56 and initiating a contact switch as has been discussed. Simultaneously, the polarization voltage is applied across contactors 36 and 34 to provide a current flow which is continually measured from the time that lid 40 is closed. A current path is formed from ring 36 through insulated nickel wire 24 to the platinum surface formed on an end of insulated nickel wire 24 and then back through silver chlorided tube 26 and contactor 34. At the surface of the platinum plated end of wire 24, polarization occurs and there is a separatization of ions resulting in the fact that only oxygen can then contribute to the current flow after the polarization occurs. By conversion of the current flow to a voltage by passage through a known value resistance, the amount of oxygen may be measured.

Prior to a discussion of the electronic circuitry utilized for control and measuring purposes an overall chronological actuation procedure is described in following sentences. Initially, bulb sensor or oxygen sensing electrode 12 is inserted within positioning lock 46 while lid 40 is in the open position. Lid 40 is closed and is mechanically maintained in a closed position through mechanicl latch 74 as seen in FIG. 1 and not important to the inventive concept as is herein described. Closure of lid 40 causes contactor 38 to actuate a switch mechanism to initiate heater, thermostatic control, and appropriate electrical circuitry to provide the measurements of partial oxygen pressure of fluid sample contained within chamber 22 of bulb sensor 12. Upon closure of lid 40 display 16 remains blank with only an indicating indicia such as a plus sign to show that system 10 is in operation. When lid 40 is closed a reset is sent through system 10 in order to set all of the counters to zero and initiate the measuring cycle time. It has been found that approximately 18-20 seconds are needed in order to bring the temperature of the fluid sample to a predetermined temperature of approximately 37° C. During this time interval display 16 is blank, however, readings are constantly being taken but not displayed. At the end of a predetermined time interval, such as 20 seconds, the final reading that was recorded during the intermediate time interval when display 16 was blank is then held and display 16 is turned on so that a steady state number appears on the output. This number is a locked number and does not vary. The timing circuitry, as will be described in following paragraphs allows the user twenty seconds within which to record the number which is generally shown in millimeters of mercury. At the end of the twenty second read-out time interval period, the heater and thermostatic control assembly 50 is caused to shut down in order to conserve power. When assembly 50 is shut down and temperature drops within chamber 22 an additional circuit senses the temperature drop and display 16 is automatically blanked. Additionally, a warning light may be added to housing 14 such that a visual display may be given to the user to open lid 40 through latch release 76. Bulb sensor 12 is then removed from positioning block 46 subsequent to the readings being taken.

Figure 8:
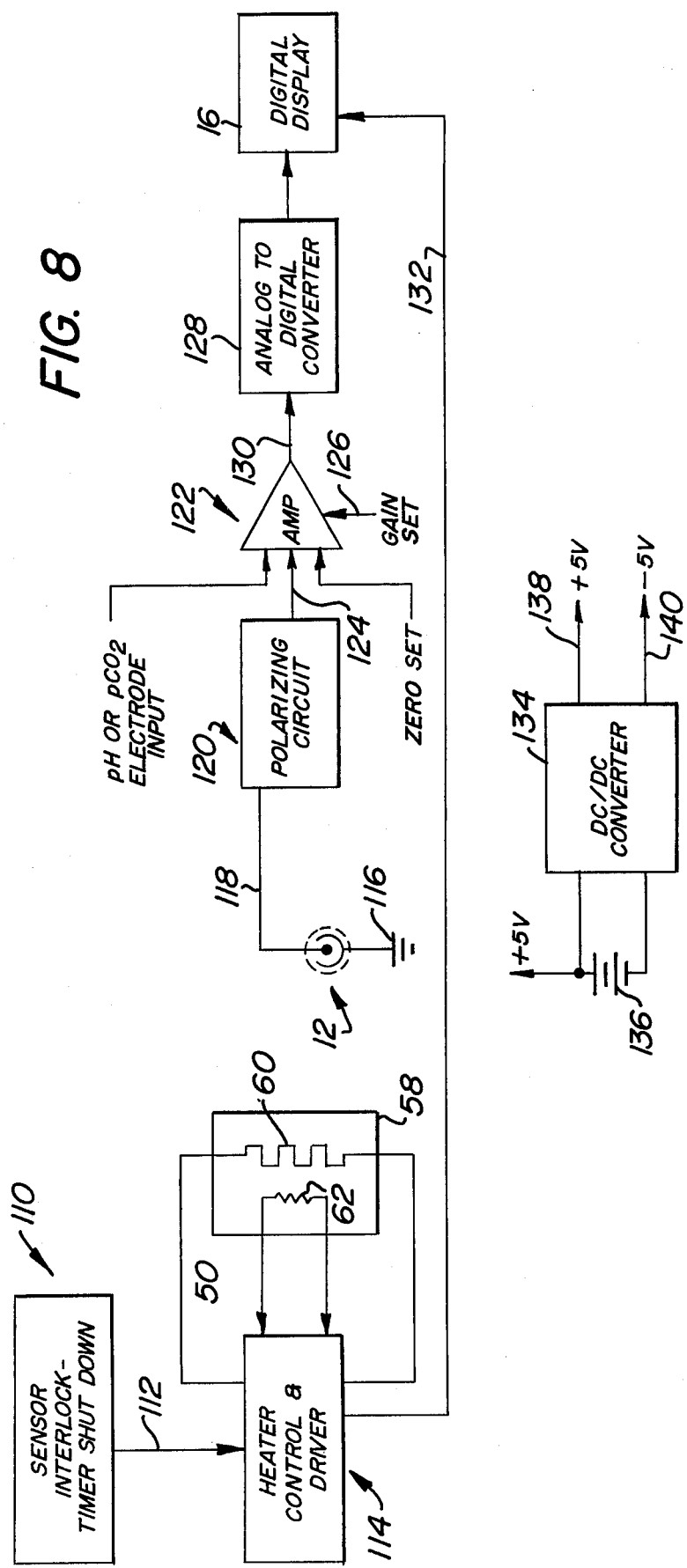
FIG. 8 is a block diagram of the overall electrical circuitry for the fluid measuring system.

Referring now to FIG. 8 there is shown the overall schematic block diagram for oxygen analyzing system 10. Block 110 is the sensor heater interlock and timer shut down logic of system 10. As will be seen in following paragraphs, the logic of block 10 primarily: (1) initiates actuation of oxygen analyzing system 10; (2) resets system 10 upon conditions to be further described; (3) provides timing pulses and counting circuitry; and (4) provides for interlocks in the event that temperature is not at a predetermined point in order to blank display 16.

Sensor interlock block 110 is coupled to heater and thermostatic control assembly 50 through line 112. Heater and thermostatic control assembly 50 includes the physical components including foil member 58 and heater and resistance thermometer wires 60 and 62 respectively as has hereinbefore been described. Additionally, the circuitry of heater and thermostatic control assembly 50 includes heater control and driver circuitry within block 114 having the basic amplifier and associated driver networks to maintain thermostatically set temperatures.

Oxygen sensing electrode 12 is maintained adjacent heater and thermostatic control assembly 50 within system housing 14 as has been previously described. As is shown in FIG. 8, bulb sensor or sensing electrode 12 is coupled to ground 116 and to polarizing circuit block 120 through line 118. Polarizing circuit block 120 includes a single mercury cell which provides a stable voltage of approximately 0.7 volts that essentially forms the bias potential for electrode sensor 12 through contactors 34 and 36 as has hereinbefore been described.

Output from polarizing circuit 120 is inserted to amplifier 122 through input line 124. Amplifier 122 is the current to voltage amplifier which has appropriate gain controls to scale the output voltage in order that such may be read in display 16 in mm. of mercury. The gain set in input to amplifier 122 through line 126 in a manner well known in the art.

Output from amplifier 122 is input to analog to digital converter 128 through line 130 and functions in conjunction with digital display 16 in order to convert the voltage appearing at the output of amplifier 50 to a digital format and then to either a light emitting diode display or to any other appropriate numerical representation not important to the inventive concept as is herein described.

As further can be seen in FIG. 8, heater control and driver block 114 is directly connected to digital display 16 through line 132 which in turn can inhibit display 16 and blank such display if the predetermined temperature is not sensed.

Figure 7A:
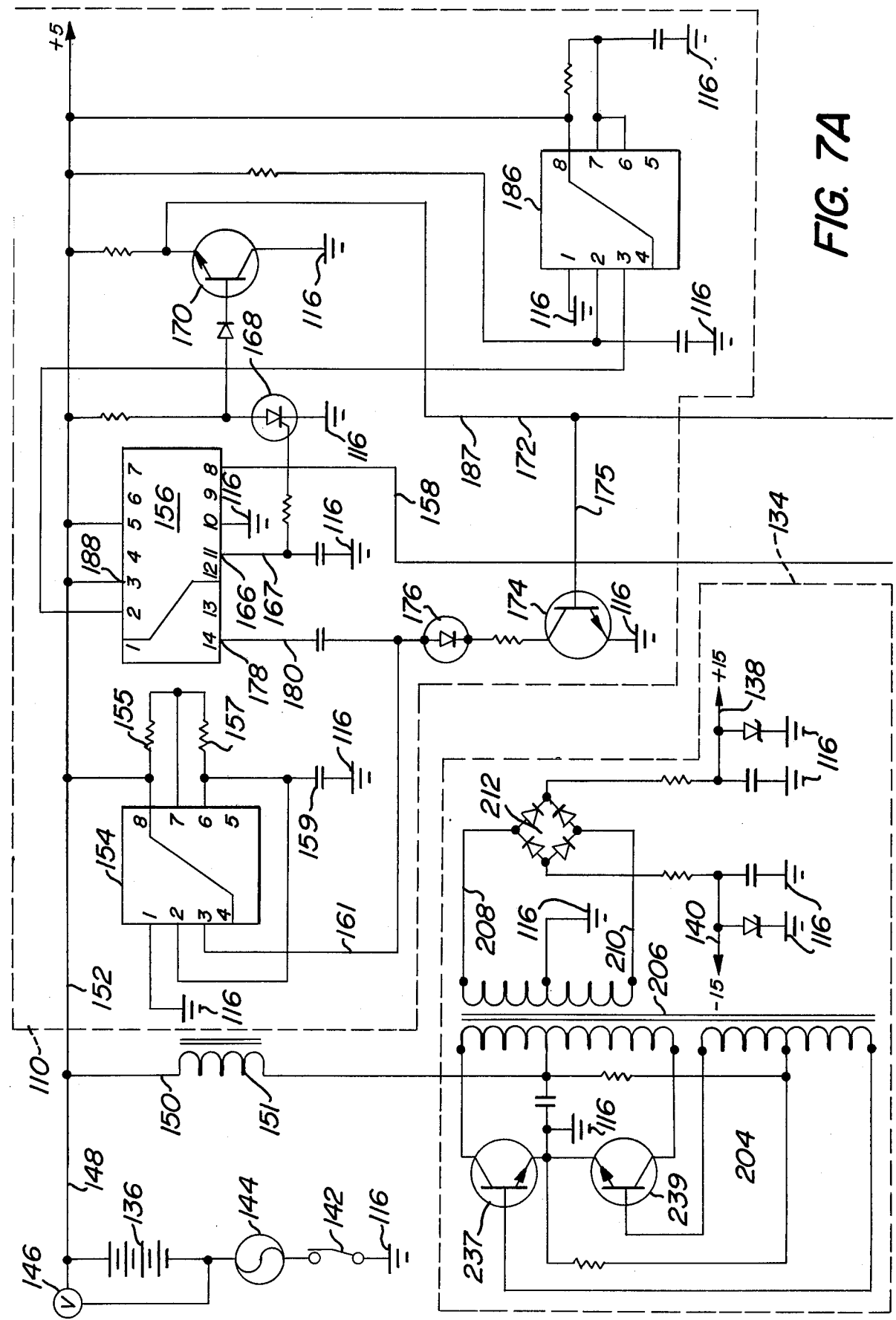
FIG. 7A is a schematic drawing of the electrical circuitry for the fluid measuring system.
Figure 7B:
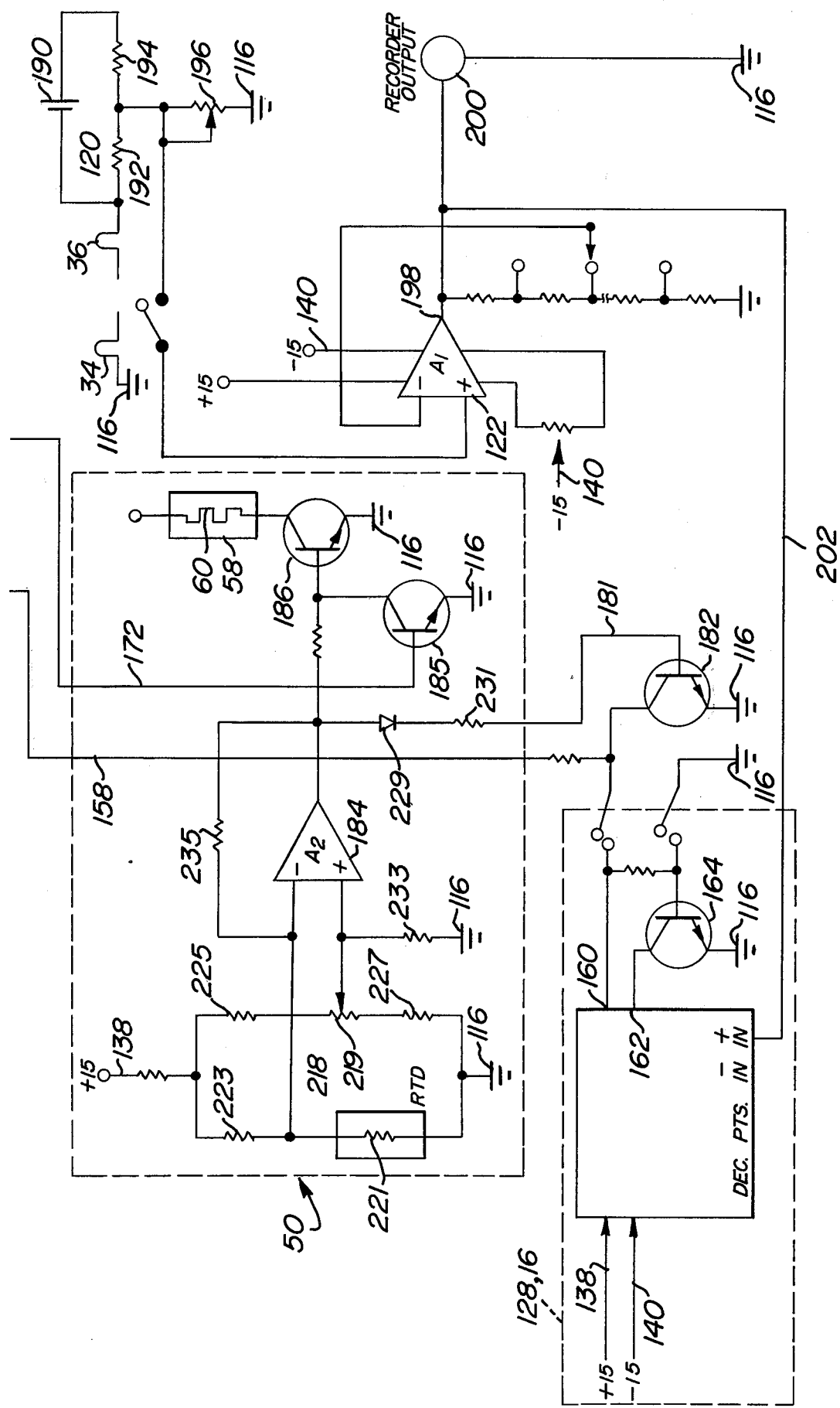
FIG. 7B is a schematic drawing of a portion of the electrical drawing electrical circuitry of the fluid measuring system.

DC/DC converter block 134 as shown in FIG. 8 in overall concept and more fully described in FIGS. 7A and 7B has as its main purpose to accept voltage from a stack of nickel cadmium batteries 136 and provide a plus and minus output of 15 volts on lines 138 and 140. Output on lines 138 and 140 is required for the analog to digital converter system and for the various operational amplifiers that are contained throughout the logic circuitry of oxygen analyzing system 10 as will be described in following paragraphs.

Referring now to FIGS. 7A and 7B there is provided the detailed logic circuitry shown in schematic form for the overall block diagram provided in FIG. 8. Initially, actuation of oxygen analyzing system 10 circuitry is provided for by electrode pressure switch 142 which is coupled to nickel cadmium batteries 136 and ground 116 through fuse element 144. Closure of lid 40 forces contactor 38 into abutting relation with actuation switch 142 which in turn closes. This initiates current flow throughout the entire circuit of system 10. Battery stack 136 is coupled in parallel relation to charger unit 146 as is shown and not important to the inventive concept as is herein described. Closure of pressure switch 142 provides for current flow in lines 148, 150 and 152 leading into sensor interlock and timer shut down block 110. As is seen, line 150 couples batteries 136 to DC/DC converter block 134 through filter indicator 151 for removal of any high frequency noise.

Overall sensor interlock and timer block 110 includes a standard 555 timer integrated circuit 154 which operates as a system clock. Such integrated circuits are well known in the art, and as provided in FIG. 7A, such is configured to run as an astable miltivibrator which has a rate output pulse of approximately 0.5 pulses per second and becomes the clock for oxygen analyzing system 10. Resistors 155 and 157 are coupled with capacitor 159 to provide the predetermined pulse rate of element 154. In order to obtain the approximate 0.5 pulse rate, resistors 155 and 157 have been used successfully in the 1.0 megaohm range and capacitor 159 is approximately 1 microfarad.

Output from timer integrated circuit 154 is fed into 7493 binary counter 156 through line 161. Counter 156 serves to divide the clock rate from 0.5 pulses per second into an output pulse occurring at 16 second intervals on line 158 and another pulse occurring at 32 second time intervals on line 167 at pin 166. These output pulses from binary counter 156 form the main timing pulses for the remainder of the oxygen analyzing system circuitry after clock 154 is counted in a manner such that the divide by eight output has changed state, which in turn allows display 16 to become visually readable and at the same time hold such display 16 at a value occurring prior to that point in time.

Thus, such essentially locks up and holds the analog/-digital converter reading at a predetermined point. In particular, the output of counter 156 at pin 8 passes through line 158 into analog/digital converter 128 and digital display 16 which essentially unblanks display 16 and latches the last converter value for display 16. Input through line 158 into converter 128 is through block contact 160 and the display hold is provided by contact 162 feeding into transistor 164 which inverts the signal at that point.

Thus, there is provided approximately 16 seconds for display and the display continues to indicate a number as the count progresses. When a pulse count reaches the 32 second point, contact 166 corresponding to pin 11 of binary counter 156 changes state. The changing of state of pin 11 triggers SCR 168 which causes that rectifier to conduct and such will remain in a conducting mode independent of the state of the timer from that point on.

As SCR 168 is forced into the conducting mode, a signal is passed through transistor 170 and line 172 into transistor 174 on line 175. Transistor 174 actuates the Remove Sensor light emitting diode 176 denoting to the operator that the test is complete and any further readings will be in error. When SCR 168 conducts, it inhibits the heater drive circuit including element 185 causing the display to blank by virtue of the temperature interlock circuit 186 and drives transistor 174 into an on condition which allows direct clock pulses from line 161 to operate light emitting diode 176.

Thus, the signal is fed or input on line 172 to transistor 185 which shorts out any heater control signals being input from amplifier 184 shown in FIG. 7B within heater control and driver block 50. This causes heater assembly block 50 to shut down and temperature, within chamber 22, begins to drop. As the temperature begins to fall, the error signal appears at the output of amplifier 184 and in turn is fed back on line 181 to transistor 182 which conducts and blanks display 16. Diode 229 on line 181 provides an offset between the bias of elements 186 and 182 in order to prevent premature shut down of the display. Diode 229 is resistance coupled to transistor 182 through resistor element 231. Resistors 233 and 235 have substantially the same values and aid in determining the loop gains of the temperature control system.

Monostable multivibrator 186 is the system reset which is initiated only upon pressure switch 142 closure. Multivibrator 186 generates a single pulse as the power is applied to the unit by closure of switch 142. This pulse on line 187 is of sufficient length to keep counter 156 in the reset mode until any start up transient voltages have subsided and therefore insures that the count begins from zero for each test cycle.

The polarizing circuit block 120 includes a 1.4 volt mercury battery 190 shown in FIG. 7B. Battery 190 is isolated from all other voltage supply in system 10 and serves to provide system 10 with the bias voltage by dividing its output in half with resistor chain elements 192 and 194 as is shown. It is to be noted that this particular circuit is in an operating mode at all times whether system 10 is an on or an off mode in order to provide a stable non-changing voltage.

Current to voltage converter amplifier 122 is a voltage follower reading the voltage drop created across load resistor 196. Load resistor 196 is generally calibrated to approximately one megohm and is the element through which the electrode or sensor current passes. Therefore, the voltage drop across resistor 196 is proportional to the current which is flowing through oxygen sensing electrode 12.

An can be seen in the FIG. 7B, the magnitude of the voltage is adjustable to provide a scale factor adjustment by the magnitude of resistance 196. The voltage is then read by amplifier 122, the gain being settable at various increments as can be seen in FIG. 7B and can be set by the operator through switch 189 shown in FIG. 1A. The output 198 from amplifier 122 goes to recorder element 200 that provides a 1 mv/mmHg output for external recording. Further, the output on line 198 is brought through line 202 into analog to digital converter and display blocks 128 and 16 which is essentially the digital display module. In essence, blocks 128 and 16 is merely a converted commercially available meter which is an analog to digital converter section and display unit. Commercially available as Analogic 2538 unit.

Referring now to FIG. 7A there is shown DC to DC converter section 134 which includes self-excited oscillator 204 comprising transistors 237, and 239 coupled to transformer 206 of the standard type and well known in the art. Oscillator 204 drives the torroidal transformer 206 that is used to convert the five volt input on line 150 into a plus and minus 15 volts exiting on lines 140 and 138. As is seen, output of transformer 206 exits on lines 208 and 210 which is DC rectified and split in bridge circuit 212. Output of bridge 212 provides for the plus and minus of 15 volt potentials on the lines 138 and 140.

Thermostatic control block 50 shown in FIG. 7B is basically a wheatstone bridge 218 which includes an internal temperature set point at some predetermined temperature. For use in blood samples, the predetermined set point provided by potentiometer 219 is 37° C. Wheatstone bridge 218 is standardly comprised of resistors 223, 225, 227, RTD resistor 221 acting in combination with potentiometer 219 for input to amplifier 184.

System 218 is a null balance system and deviation is amplified through amplifier 184, the output of which is fed to transistor 186 which controls the current in heater foil member 58 and associated heater wires 60.

What is claimed is:

1. A fluid measuring system for quantitating the amount of particular constituents contained in a fluid, comprising:
    (a) sensor means having a chamber adapted to contain said fluid, said sensor means having anode electrode means extending internal said chamber within said sensor means, and, cathode electrode means extending internal said chamber and said anode electrode means;

(b) housing means for insert of said sensor means in predetermined positional relationship therewith;

(c) thermostatic control means within said housing means for heating and maintaining said fluid within said chamber at a predetermined temperature; and, (d) means for applying current to said sensor means and said thermostatic control means for measurement of the amount of said particular constituents contained in said fluid.

2. The fluid measuring system as recited in claim 1 where said cathode electrode means extends co-axial with said anode electrode means.

3. The fluid measuring system as recited in claim 1 where said sensor means includes a glass tube member extending in a longitudinal direction, said anode and cathode electrode means being positionally located internal said tube member.

4. The fluid measuring system as recited in claim 1 where said cathode electrode means includes an insulated electrically conductive wire member.

5. The fluid measuring system as recited in claim 1 where said anode electrode means includes a silver tube member, said silver tube member having a chloride coating on an outer wall surface.

6. The fluid measuring system as recited in claim 1 where said anode and said cathode electrode means are mounted within an epoxy resin element located within said chamber.

7. The fluid measuring system as recited in claim 6 where said epoxy resin element includes an end face surface in a plane substantially normal to said extensions of said anode and said cathode electrode means.

8. The fluid measuring system as recited in claim 7 where said cathode electrode means extends to said end face surface, said cathode electrode means forming an end surface co-planar with said epoxy resin element end face surface.

9. The fluid measuring system as recited in claim 8 where said cathode electrode means end surface is plated with a platinum polarizing composition adapted to be in communication with said fluid having dissolved oxygen formed therein.

10. The fluid measuring system as recited in claim 9 where said polarizing composition is platinum.

11. The fluid measuring system as recited in claim 1 where said anode and cathode electrode means extend external said sensor means.

12. The fluid measuring system as recited in claim 11 where said sensor means includes:

(a) a first electrical contact member coupled to said anode electrode means; and, (b) a second electrical contact member coupled to said cathode electrode means, said first and second electrical contact members being mounted to an outer wall of said sensor means.

13. The fluid measuring system as recited in claim 12 including a third electrical contact member for initiating said thermostatic control means and said current application means subsequent to said insertion of said sensor means within said housing means.

14. The fluid measuring system as recited in claim 1 where said sensor means includes means for drawing said fluid internal said chamber of said sensor means, said fluid drawing means being mounted to a first end of said sensor means.

15. The fluid measuring system as recited in claim 14 where said fluid drawing means includes a resilient bulb element mounted to said first end of said sensor means.

16. The fluid measuring system as recited in claim 15 including a cap element releasably secured to a second end of said sensor means opposing said first end for maintaining a closed volume chamber within said sensor means.

17. The fluid measuring system as recited in claim 1 where said housing means includes sensor positioning means for inserting said sensor means in predetermined positional relationship therewith.

18. The fluid measuring system as recited in claim 17 where said positioning means includes a block member having a well formed therein for receiving said thermostatic control means.

19. The fluid measuring system as recited in claim 18 where said block member includes a plurality of apertures formed therein for receiving a plurality of electrical contact elements secured to an outer wall of said sensor means.

20. The fluid measuring system as recited in claim 17 where said housing means includes a lid member rotatably mounted to an outer wall of said housing means, said lid member being displaceable for contacting said sensor means when said sensor means is inserted within said housing means.

21. The fluid measuring system as recited in claim 17 where said housing means includes display means for displaying a digital representation of a proportional current of said applied current to said sensor means.

22. The fluid measuring system as recited in claim 17 where said thermostatic control means includes heater mounting means inserted within a well formed within a positioning block of said housing means.

23. The fluid measuring system as recited in claim 22 where said heater mounting means includes a flexible foil member, said flexible foil member having an inverted omega contour adapted to receive said sensor means.

24. The fluid measuring system as recited in claim 23 where said flexible foil member is adapted to be compressively deformed into contiguous relation with a predetermined segmental surface area of a stem portion of said sensor means responsive to a closure of a lid member of said housing means.

25. The fluid measuring system as recited in claim 23 where said flexible foil member includes a pair of transversely opposing vertically directed wall members extending above a stem portion of said sensor means when said sensor means is inserted within a recess between said vertically directed wall members.

26. The fluid measuring system as recited in claim 25 where said housing means includes a lid member adapted to contact an upper portion of said sensor means for deflecting said wall member upper portions into contiguous contact with a predetermined segment of said stem of said sensor means.

27. The fluid measuring system as recited in claim 23 where said heater mounting means includes heater elements inserted within said flexible foil member, said heater elements passing in an undulating fashion when taken with respect to a longitudinal extension of said foil member.

28. The fluid measuring system as recited in claim 27 where said heater mounting means includes resistor thermometer wire elements inserted within said foil member for sensing the temperature of fluid contained within a steam portion of said sensor means.

29. The fluid measuring system as recited in claim 28 where said resistor thermometer elements pass in an undulating manner when taken with respect to said longitudinal extension of said foil member.

30. The fluid measuring system as recited in claim 29 where said heater elements and said resistor thermometer elements alternate in positional location when taken each with respect to the other within said foil member.

31. The fluid measuring system as recited in claim 1 where said current application means includes:
 (a) electrical circuit means for heating and maintaining a predetermined temperature of said fluid within said sensor means;
 (b) means for applying a predetermined voltage to said sensor means; and,
 (c) means for indicating a predetermined current value proportional to said current flow through said sensor means.

32. A fluid measuring sensor comprising:
 (a) an enclosed glass tubular housing extending in a longitudinal direction forming an internal chamber adapted to contain a fluid; said housing including a resilient bulb element mounted to one end of said housing for drawing fluid internal said chamber;
 (b) anode electrode means extending internal said housing in said longitudinal direction; and,
 (c) cathode electrode means extending in said longitudinal direction internal said housing and said anode electrode means.

33. The fluid measuring sensor as recited in claim 32 wherein said bulb element is releasably secured to said glass tube member.

34. The fluid measuring sensor as recited in claim 33 where said housing includes a cap element releasably secured to one of said opposing longitudinal ends of said housing.

35. The fluid measuring sensor as recited in claim 32 where said anode electrode means includes a tubular member extending in said longitudinal direction within said housing.

36. The fluid measuring sensor as recited in claim 35 where said tubular member extends external said housing.

37. The fluid measuring sensor as recited in claim 36 where said tubular member is secured to a first electrical contact ring element external said housing.

38. The fluid measuring sensor as recited in claim 37 where said first electrical contact ring element is secured to an outer wall of said housing.

39. The fluid measuring sensor as recited in claim 38 where said tubular member is formed of an electrically conductive material.

40. The fluid measuring sensor as recited in claim 39 where said tubular member electrically conductive material is silver.

41. The fluid measuring sensor as recited in claim 40 where said silver tube member is chloride coated on an outer wall surface.

42. The fluid measuring sensor as recited in claim 32 where said cathode electrode means extends co-axial with said anode electrode means.

43. The fluid measuring sensor as recited in claim 42 where said cathode electrode means includes an insulated electrically conductive wire member.

44. The fluid measuring sensor as recited in claim 43 where said cathode wire member extends external to said housing.

45. The fluid measuring sensor as recited in claim 44 where said conductive wire member is secured to a second electrical contact ring element external said housing.

46. The fluid measuring sensor as recited in claim 45 where said second electrical contact ring element is secured to an outer wall of said housing.

47. The fluid measuring sensor as recited in claim 32 where said anode and said cathode electrode means are mounted within an epoxy resin element positionally located within said internal chamber.

48. The fluid measuring sensor as recited in claim 47 where said epoxy resin element includes an end face surface in a plane substantially normal to said extensions of said anode and said cathode electrode means.

49. The fluid measuring sensor as recited in claim 48 where said cathode electrode means extends to said end face surface, said cathode electrode means forming an end surface substantially co-planar with said epoxy resin element end face surface.

50. The fluid measuring sensor as recited in claim 49 where said cathode electrode means end surface is plated with a platinum polarizing composition.

51. The fluid measuring sensor as recited in claim 50 where said polarizing composition is platinum.

52. A fluid measuring thermostatic control assembly adapted to heat and maintain a fluid contained within a fluid measuring sensor to a predetermined temperature, comprising:
 (a) heater mounting means adapted to receive said fluid measuring sensor; said heater mounting means including a flexible foil member having an inverted Omega contour deformable into contiguous relation with a predetermined segmental surface area of a stem portion of said fluid measuring sensor, said flexible foil member having heater elements contained therein passing in an undulating manner when taken with respect to a longitudinal extension of said foil member and
 (b) electrical circuit means coupled to said heater mounting means for heating and maintaining said predetermined temperature of said fluid within said sensor.

53. The fluid measuring thermostatic control assembly as recited in claim 52 where said heater mounting means includes resistor thermometer wire elements inserted within said foil member for sensing said temperature of said fluid contained within said stem portion of said fluid measuring sensor.

54. The fluid measuring thermostatic control assembly as recited in claim 53 where said resistor thermometer elements extend in an undulating manner when taken with respect to said longitudinal extension of said foil member.

55. The fluid measuring thermostatic control assembly as recited in claim 54 where said heater elements and said resistor elements alternate in positional location when taken each with respect to the other within said foil member.

* * * * *